United States Patent [19]

Cox et al.

[11] 4,206,754
[45] Jun. 10, 1980

[54] LUNG VENTILATORS

[75] Inventors: Lawrence A. Cox, Epping; John D. Smethers, Wormley, both of England

[73] Assignee: BOC Limited, London, England

[21] Appl. No.: 799,985

[22] Filed: May 24, 1977

[30] Foreign Application Priority Data

Jun. 2, 1976 [GB] United Kingdom ............ 22706/76

[51] Int. Cl.² ............................................ A61M 16/00
[52] U.S. Cl. ........................ 128/204.21; 128/204.26; 128/205.11
[58] Field of Search ............... 128/145.8, 145.6, 145.5, 128/188, 142.2

[56] References Cited

U.S. PATENT DOCUMENTS

| | | | |
|---|---|---|---|
| 3,768,468 | 10/1973 | Cox | 128/145.8 |
| 3,905,362 | 9/1975 | Eyrick et al. | 128/145.8 |
| 3,967,619 | 7/1976 | Story et al. | 128/145.8 |
| 3,974,828 | 8/1976 | Bird | 128/145.8 |
| 4,020,834 | 5/1977 | Bird | 128/145.6 |
| 4,060,078 | 11/1977 | Bird | 128/145.8 |

Primary Examiner—Henry J. Recla
Attorney, Agent, or Firm—Dennison, Dennison, Meserole & Pollack

[57] ABSTRACT

A volume-cycled lung ventilator providing for both spontaneous breathing of a patient and intermittent mandatory ventilation, the invention provides two parallel inspiratory flow paths, one flow path including a demand valve for supplying gas to the patient during spontaneous breathing and the other flow path including a solenoid-operated inspiratory flow valve for providing intermittent mandatory breaths. The invention provides structure capable of adjusting the intervals between mandatory breaths, the volume of each such breath and the flow waveform of each such breath. An expiratory flow path including a fluid operated expiratory flow valve is further provided. A flow rate signal generator in the expiratory flow path acts to sense the rate of exhalation of the patient and is effective to inhibit the opening of the inspiratory flow valve unless the rate of exhalation is below a predetermined value.

2 Claims, 1 Drawing Figure

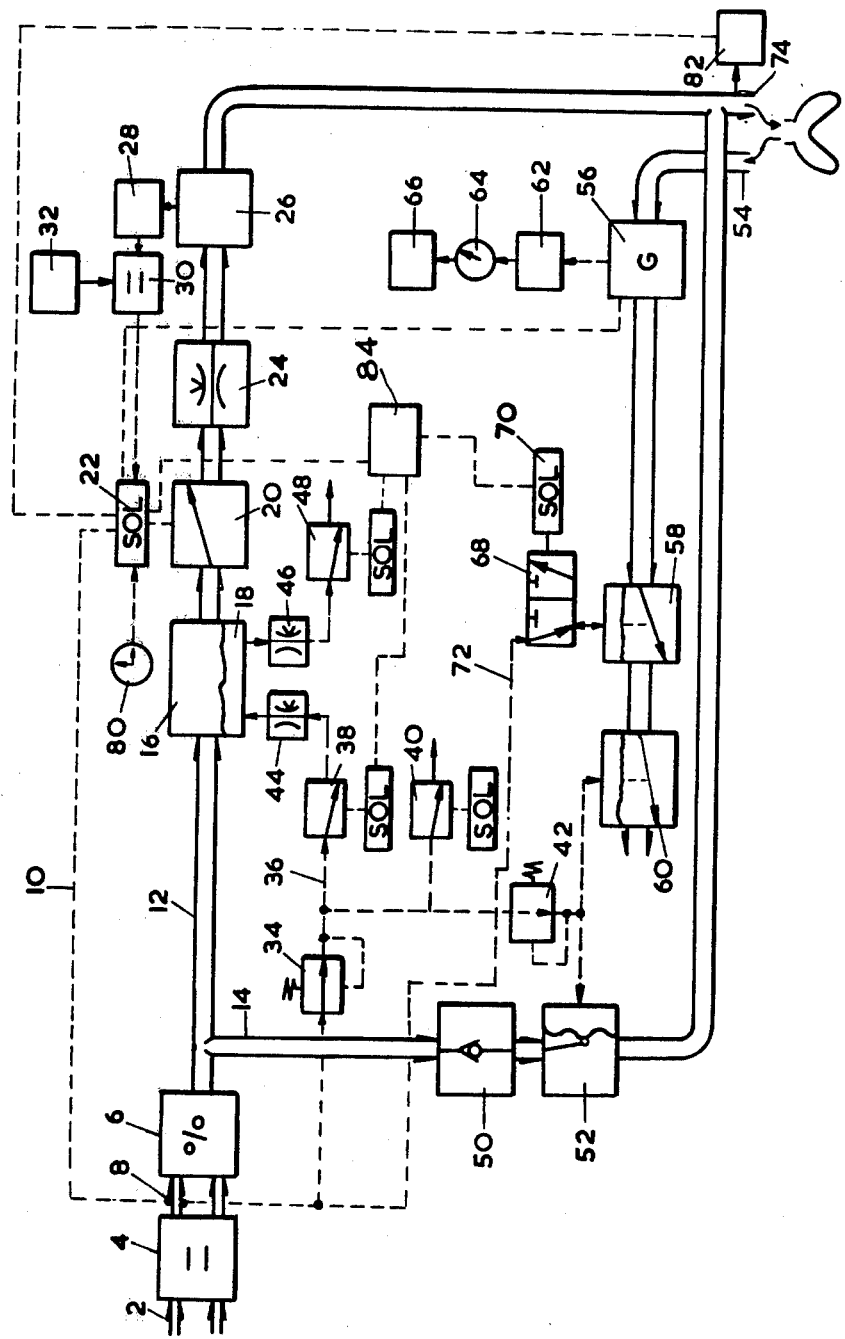

LUNG VENTILATORS

This invention relates to lung ventilators, which are devices intending to be connected to a patient's airway, as by means of a mask or endotracheal tube, to augment or replace the patient's ventilation automatically.

DESCRIPTION OF THE PRIOR ART

Lung ventilators are known wherein respirable gas is fed automatically to a patient until he starts to breathe spontaneously, the gas flow paths for spontaneous and automatic ventilation being discrete flow lines.

One of the difficulties associated with the use of lung ventilators is the necessity to wean patients from them so that they can breathe spontaneously. This difficulty has been largely overcome by providing lung ventilators with an intermittent mandatory ventilation (IMV) mode, by which is meant that the ventilator is designed to go through a forced or 'mandatory' ventilation cycle at suitably-spaced intervals chosen by an operator, whilst permitting the patient to breathe spontaneously, i.e. without assistance, during the intervening periods. At the start of the weaning process, these IMV cycles are closely matched to the patient's spontaneous breathing rate, but gradually the interval between the IMV cycles is increased so that the IMV cycles become separated from each other by one or several spontaneous breaths, the number of such breaths being increased as the weaning process continues, until the IMV 'breaths' have negligible beneficial effect on the patient, enabling the ventilator to be disconnected from the patient who by now is able to breathe spontaneously and unassisted.

Hitherto, no fully satisfactory lung ventilators having an IMV mode have been developed; rather, the tendency has been to convert existing lung ventilators to have an additional IMV mode.

SUMMARY OF THE PRESENT INVENTION

Accordingly, the present invention provides a volume-cycled lung ventilator providing for both spontaneous breathing of a patient connected thereto, and intermittent mandatory ventilation, the ventilator having a first inlet for respirable gas, a first outlet for supplying respirable gas to a patient, a second inlet for gas expired by the patient, a second outlet for venting the expired gas to atmosphere, two gas flow paths extending in parallel with each other between the first inlet and the first outlet, in which one of the gas flow paths includes an adjustably-biased demand valve for supplying gas to the first outlet when the gas pressure thereat falls to a preset value, and in which the other of the gas flow paths includes means for supplying to the first outlet at adjustable intervals an adjustable volume of gas having an adjustable flow waveform.

By "volume-cycled" is meant a ventilator which includes a flow-measuring device arranged to integrate the gas volume supplied to the patient during each inspiratory phase and to stop the flow of gas when the measured volume reaches a chosen minimum value.

According to a preferred feature of the present invention, the ventilator includes means for inhibiting the supply of the timed volume of gas until after the rate at which the patient is expiring gas falls to below a chosen value of flowrate.

BRIEF DESCRIPTION OF THE DRAWING

The present invention will now be described by way of example with reference to the accompanying drawing, which is a schema of a lung ventilator according to the present invention.

DESCRIPTION OF THE PREFERRED EMBODIMENT

The lung ventilator has a main inlet, indicated diagramatically at 2, which is intended to be supplied with oxygen and air at a suitable pressure. In this specification, the term 'air' is going to be referred to as a gas, for grammatical reasons, rather than as a mixture of gases. The two gases pass to a balancer 4 in which the pressures of the two gases are equalised, although the two gases are kept separate from each other. From the balancer, the gases flow to an adjustable mixer 6, in which the proportion of oxygen in the output from the mixer (which is eventually supplied to the patient) can be varied between 0% and 100%. Although the ventilator could theoretically still work if there were no added oxygen, in practice, for safety reasons, the ventilator ceases working if the supply of either gas fails.

Prior to the mixer 6 the pressurised oxygen passes to a junction 8, from which part is taken off through a control line 10 for control purposes to be described below, and the rest of which flows to the mixer 6, from which the desired gas mixtures flow into two alternative flow paths 12 and 14.

The gas pressures at the upstream ends of flow paths 12 and 14 are equal.

Positioned in flow path 12 is a flow waveform regulator 16 including a gas-tight chamber 18 which can be pressurised to varying degrees, by means described below, so as to alter the output pressure of regulator 16 in a manner which varies with time, thereby altering the flow waveform of gas leaving regulator 16. This gas passes to an inspiratory flow valve 20 controlled by a solenoid 22 of which the working fluid is derived from control line 10. When valve 20 is open, the gas passes through an adjustable needle valve 24 and an inspiratory flow signal generator 26 designed to generate electrical signals which are a function of the instantaneous rate at which gas is flowing through generator 26. Preferably, the signals are in the form of a series of pulses, with each pulse corresponding to the passage through the generator 26 of a unit volume of respirable gas. This form of signal ensures that the actual volume of gas which has been supplied to a patient during each inspiratory phase can be calculated by counting the number of pulses, knowing the unit volume per pulse. Diagrammatic means for producing this are shown in the schema, in which reference 28 is to an integrator adapted to count the incoming pulses from signal generator 26 and supply them to a comparator 30 having as a second input a signal from a presettable device 32 for choosing the volume of gas which is to be supplied to the patient during each mandatory inspiratory phase. The comparator 30 is connected to a solenoid 22 so that when the measured value is equal to the preset value the comparator causes the solenoid 22 to close the inspiratory flow valve 20, thus marking the end of the respective inspiratory phase.

From generator 26 the respirable gas flows via line 74 directly to a mask, endotracheal tube or like device for supplying gas to the lungs (as indicated diagrammatically) of a patient.

Connected to junction 8 is a pressure regulator 34 designed to produce a pressure of about 20 psig in a control line 36 to which are connected two solenoid-operated valves 38 and 40, and a low-pressure regulator 42 designed to give an adjustable outlet pressure up to 200 mm of water.

The valve 38 is connected through an adjustable needle valve 44 with chamber 18, which is in turn connected through a second adjustable needle valve 46 to a solenoid-operated valve 48 adapted to vent to atmosphere when the valve is operated. The solenoids controlling valves 38 and 48 are operated sequentially when it is desired to give a rising or falling slope to the curve of flow rate produced by regulator 16. When the flow rate is intended to remain uniform during the respective inspiratory phase, valve 38 is opened and valve 48 is closed so that the pressure in chamber 18 remains constant. This ensures that gas leaves regulator 16 at a constant rate depending upon the setting of needle valve 24. When a wave form with a rising slope is required, the valve 48 is opened during each expiratory phase so as to vent to atmosphere all the gas in chamber 18. At the beginning of each inspiratory phase, the valve 48 is closed and valve 38 opened to permit gas to flow slowly into chamber 18 from junction 8 through needle valve 44. The resultant increase in pressure in chamber 18 causes a corresponding increase in output pressure of regulator 16 so that the flow through valve 24 gradually increases, thus giving the required waveform. At the end of the inspiratory phase, the valve 38 is closed and then valve 48 is opened to restore the desired initial conditions for the beginning of the next inspiratory phase.

When a waveform having a falling slope is required, the valves are operated in the same sequence but during opposite phases of the respiratory cycle. In other words, the chamber 18 is full at the start of an inspiratory phase, at which time the inspiratory flow valve 20 is closed, and is allowed to vent slowly to atmosphere through valves 46 and 48 during each inspiratory phase, but valve 38 is still left open so that the pressure in chamber 18 does not fall to zero, but to a stable pressure dependent on the settings of needle valves 44 and 46, thus reducing the rate at which gas flows through valve 20 and needle valve 24.

The means 84 by which operation of the respective solenoids is timed with respect to the respiratory cycle do not in themselves form part of the subject-matter of this invention and so are not further described herein.

When valve 40 is operated, which takes place during the expiratory phase, gas is supplied to a venturi device or like aspirator for applying to the lungs of the patient a pressure below atmospheric. In the art of lung ventilators, the resultant sub-atmospheric pressure is referred to as 'negative pressure' or 'negative phase'. The means by which the negative pressure device works, and is timed with respect to the patient's respiratory cycle, are known in themselves and so are not further described in this specification.

Positioned in cascade in flow path 14 are an isolation valve 50 and a fluid-biased demand valve 52 designed to act as a patient-operated valve for supporting attempts by the patient at spontaneous respiration. The outlet of valve 52 is connected to the patient's mask or like gas-supplying device. This ensures that the patient can receive gas alternatively either from the mandatory respiration device effectively forming flow path 12, or from the patient-operated gas flow path 14.

The lung ventilator also includes an exhaust flow path 54 through which the patient can exhale exhausted gases. The path 54 contains an expiratory flow signal generator 56 similar to the inspiratory generator 26. Positioned downstream of generator 56 are a fluid-biased expiratory valve 58 and an adjustably-biased PEEP valve 60, the term 'PEEP' standing for 'positive end-expiratory pressure'.

The generator 56 supplies signals to an integrator 62 driving a minute-volume meter 64 coupled to an alarm 66. The meter 64 has a presettable contact associated with it so that when the measured minute-volume falls below a chosen threshold value, indicating that the patient has ceased to breathe out a satisfactory volume of gas, the alarm 66 is actuated to draw attention to the situation. The means by which the alarm 66 and meter 64 are reset for the beginning of the next expiratory phase are known in themselves and so are not described further in this specification.

The expiratory flow valve 58 is controlled by a two-position, three-port valve 68 controlled by a solenoid 70. By means which are not shown in the drawing or described further in this specification, de-energisation of solenoid 70, which causes closing of expiratory valve 58, is related to the time for which solenoid 22 has been previously energised to open inspiratory valve 20. In the art of lung ventilation, the operator sometimes has the power to adjust the so-called 'I/E ratio', which is the ratio of the duration of the inspiratory phase (I) compared with that of the immediately succeeding expiratory phase (E).

In one form of lung ventilator of the present invention, the operator is able to adjust this I/E ratio between values of 1:1 and 1:3. This is achieved by means 84 which are not illustrated, but which include a timer for measuring the duration of each inspiratory phase. At the close of the inspiratory phase, the solenoid 70 is energised to open the expiratory valve 58 and to keep it open for a time determined by the duration of the inspiratory phase multiplied by the chosen I/E ratio.

Because the I/E ratio control measures the duration of each individual inspiratory phase, as a prerequisite to determining the corresponding expiratory phase time, it follows that automatic compensation will occur if any alteration is made to either the inspiratory tidal volume or the mean inspiratory phase time. When such an alteration is made, the I/E ratio control automatically applies a correction to the following expiratory phase time to maintain the chosen I/E ratio correct, thus updating the cycle time breath by breath.

It will be seen, therefore, that the frequency of the respiratory cycle is a derived value, being dependent upon the preset I/E ratio and the actual inspiratory phase time, the latter being in turn dependent upon the combination of the preset inspiratory tidal volume and the mean inspiratory flow rate.

The valve 68, controlled by solenoid 70, has gas at the working pressure supplied to it from junction 8 by means of a control line 72. When solenoid 70 is energised during the inspiratory phase, the gas passes to valve 58 and biases it closed. When the solenoid 70 is de-energised, the position of valve 68 is changed to permit the chamber-biasing valve 58 to be vented to atmosphere, thus permitting valve 58 to open.

The PEEP valve 60 is adjustably biased by the regulator 42 so as to terminate expiration by the patient when the pressure in conduit 54 falls to the pressure set by the outlet pressure of regulator 42. In other words, the lowest pressure reached in conduit 54 is that determined by the setting of regulator 42. The PEEP can be set at any value up to about 200 mm of water.

This same fluid bias is applied by regulator 42 to demand valve 52, so that the threshold between the flowing and non-flowing states of the demand valve is at the same pressure as the PEEP value. This means that the demand valve 52 will remain closed while the patient is exhaling, but as soon as an attempt at respiration by the patient causes the pressure in conduit 74 to drop below the selected PEEP value, the demand valve 52 opens, allowing gas to pass to the patient at a rate dictated by the patient's inspiratory effort. Gas is supplied to demand valve 52 from the isolation valve 50 at the same rate as it is withdrawn by the patient, so that the system acts virtually as an infinite reservoir of gas available to the patient when breathing spontaneously.

By means 84 which are not described in further detail in this specification, operation of solenoid 22, and therefore the beginning of a mandatory inspiratory phase, is prevented while the patient is exhaling. This could be done by ensuring that the generation of signals by generator 56 is effective to inhibit solenoid 22. This ensures that the patient is not distressed by being forced to take a breath at a time when he is exhaling naturally.

Notwithstanding the fact that in the form of ventilator as described, the respiratory frequency is a derived value (being dependent upon inspiratory phase time and I/E ratio) a separate timer 80 is provided which under certain circumstances controls the respiratory frequency.

In accordance with the present invention, the timer 80 controlling solenoid 22 is designed to cause a mandatory respiratory cycle to be initiated at intervals which may be significantly longer than the length of a normal respiratory cycle. Thus the timer 80 could be set to give one mandatory breath at regular intervals adjustable between say two seconds and two minutes. In the art of lung ventilators, this regular and mandatory initiation of a respiratory cycle is referred to as occurring 'intermittently', which accounts for this mode of operation of the ventilator being referred to as 'intermittent mandatory ventilation' or 'IMV'.

It will be clear that the principle of the automatic I/E ratio compensation already described is not physiologically acceptable when applied to extremely low cycling frequencies, such as one or two breaths per minute, as the I/E ratio would need to be very high, say, 1:20 or 1:30. When using these lower IMV frequencies the timer 80 controlling solenoid 22 operates irrespectively of the I/E ratio compensating circuits. However, the same does not apply at the higher frequency end of the range, where a frequency may be chosen which results in a total cycle time (inspiratory plus expiratory phase times) which because of the preset inspiratory tidal volume and the preset mean inspiratory flow, does not allow the preset I/E ratio to be achieved, in which case the I/E ratio controller overrides the system and inhibits the start of inspiration, resulting in a lowering of the cycling frequency. The operator would normally compensate for this by manually changing one of the aforesaid preset values, for example by reducing the inspiratory tidal volume or by increasing the inspiratory flow rate.

Although initiation of the IMV pulse is inhibited while the patient is breathing out, there is the possibility that the pulse will start while the patient is nearing the end of the inspiratory phase of a spontaneous respiratory cycle. When the patient's lungs are full, or nearly so, it would clearly be distressing if the lung ventilator attempted to force even more gas into the patient's lungs regardless of his inability to accept more gas. To prevent this from happening, the ventilator has an override device which operates in response to the pressure in the inlet conduit 74 to the patient. When the patient's lungs are nearly full the initiation of an IMV cycle causes the pressure of the gas in his lungs to tend to increase, although virtually no further gas is able to be supplied to the patient other than that needed to raise the pressure of the gas in his lungs and to distend his lungs somewhat further, because of the higher pressure.

When this occurs, a switch 82 sensitive to the pressure in conduit 74, and therefore to that in the patient's lungs, operates to override the normal volume cycling mechanism and cause the ventilator to cycle when the pressure reaches a chosen maximum value. This is normally chosen to be slightly greater than any maximum pressure normally present in conduit 74 during mandatory ventilation. The effect of this override control is to convert the lung ventilator temporarily from its usual volume-cycled mode of operation to a conventional pressure-cycled mode. This results in the tidal volume dropping, but the I/E ratio is held.

It will be appreciated from the above that the patient can continue breathing spontaneously, by demanding gas from valve 52, immediately after the IMV pulse.

Because the IMV pulse can be applied at a frequency which is adjustable from say 30 pulses per minute (corresponding to the natural number of breaths per minute of some patients) to a frequency of 0.5 pulses per minute (corresponding to a frequency of mandatory pulses which is significantly lower than the minimum number of natural breaths drawn by any patient), it will be seen that the lung ventilator of the present invention can be adjusted, usually at discrete intervals, so as to encourage the patient's attempts at spontaneous breathing until he no longer needs the ventilator.

It is believed that the lung ventilator of the present invention is primarily successful because patients deliberately or unconsciously 'test' the ventilator by refraining from breathing at random times to check that the machine is working. They are reassured when the ventilator ignores these attempts and forces the patient to breathe at intervals which are chosen suitably with regard to the patient's natural ability to breathe spontaneously. Once the patient has been reassured that the ventilator is working normally, and can take over all responsibility for ventilating the patient should his natural efforts fail, it has been found that he is more likely to persevere with his efforts to ventilate himself normally, thus effectively weaning himself from dependence on the ventilator.

What we claim is:

1. A volume-cycled lung ventilator providing for both spontaneous breathing of a patient connected thereto and intermittent mandatory ventilation, the ventilator comprising:

means defining a first inspiratory flow path and means connecting such flow path at its inlet end to a source of pressurized respirable gas;

means defining a second inspiratory flow path and means connecting such flow path at its inlet end to the source of respirable gas;

means defining an expiratory flow path connected at its outlet end to atmosphere;

patient connection means for supplying respirable gas from the outlet ends of said first and second inspiratory flow paths to a patient, and for supplying gas expired by the patient to the inlet end of said expiratory flow path;

a normally-closed inspiratory flow valve in said first inspiratory flow path and a normally-open expiratory flow valve in said expiratory flow path;

means for operating said inspiratory and expiratory flow valves in synchronization at preselectable intervals to provide intermittent mandatory inspiration through said first inspiratory flow path and expiration through said expiratory flow path, the inspiratory flow valve being open during the inspiratory phase and the expiratory flow valve being closed during the inspiratory phase, the inspiratory flow valve being closed during the expiratory phase and the expiratory flow valve being open during the expiratory phase;

valve means in said second inspiratory flow path to permit spontaneous inspiration through such flow path while expiration is occurring through said expiratory flow path, the valve means comprising a demand valve adapted to permit gas to flow through the second inspiratory flow path from the source to the patient at a flow rate determined by the inspiratory effort of the patient, and a second expiratory valve being provided in said expiratory flow path downstream of said normally open expiratory valve and said demand valve and second expiratory valve are fluid-biased valves and include a regulator connected to the demand valve and second expiratory valve for adjustably biasing both the demand valve and the fluid-biased second expiratory valve so that the expiratory pressure required to stop the supply of gas by the demand valve to the patient is maintained substantially the same as the pressure required to open the second expiratory valve; and, means for inhibiting the opening of said inspiratory flow valve if the patient is expiring gas at a flow rate above a chosen value, the inhibiting means comprising signal generating means in said expiratory flow path for producing signals representative of the rate of flow of gas expired through said flow path, and means responsive to said signals for inhibiting the opening of said inspiratory flow valve during the exhalation phase.

2. A lung ventilator as claimed in claim 1 wherein means sensitive to pressure in the outlet end of the first inspiratory flow path are effective to close said inspiratory flow valve when said pressure reaches a preset maximum.

* * * * *